United States Patent [19]

Wang

[11] Patent Number: 4,966,162
[45] Date of Patent: Oct. 30, 1990

[54] FLEXIBLE ENCOSCOPE ASSEMBLY

[76] Inventor: Ko P. Wang, 11006 Nacirema La., Stevenson, Md. 21153

[21] Appl. No.: 301,132

[22] Filed: Jan. 25, 1989

[51] Int. Cl.$^5$ ............................................. A61B 10/00
[52] U.S. Cl. .................................... 128/750; 128/752; 128/756
[58] Field of Search ............................ 128/749–759; 15/206, 182, 104.2

[56] References Cited

U.S. PATENT DOCUMENTS

| | | | |
|---|---|---|---|
| 3,074,396 | 1/1963 | MacLean | 128/756 |
| 3,831,585 | 8/1974 | Brondy et al. | 128/757 |
| 4,227,537 | 10/1980 | Suciu et al. | 128/756 |
| 4,465,072 | 8/1984 | Taheri | 128/756 |
| 4,532,935 | 8/1985 | Wang | 128/753 |

Primary Examiner—Randall L. Green
Assistant Examiner—Randy Shay
Attorney, Agent, or Firm—Cushman, Darby & Cushman

[57] ABSTRACT

A flexible assembly for use with a fiberoptic endoscope to collect tissue specimens from a site within the human body. The assembly includes a flexible outer catheter provided with a metal tip at its distal end, a flexible stylet, and a control structure at the proximal end of the catheter to control movement of the stylet within and axially along the catheter and for the introduction of fluids to the collection site and/or withdrawal of fluids within the catheter from the collection site. The stylet has a distal end provided with a brush terminating with a needle point or a looped type end at its distal end. The brush will be movable through an incision in tissue produced by the needle point allowing penetration through the body cavity wall into a tumor or lesion located therebeyond. The stylet can also include a coiled spring for providing a flexible connection between the control structure and the tissue collection device. In addition to a brush, the tissue collection device can include a hollow needle or a pair of selectively sliding needles. Specimen samples can be obtained and local flushing of the specimen collection site is possible. Specimen material can also be flushed from within the catheter.

7 Claims, 9 Drawing Sheets

FLEXIBLE ENCOSCOPE ASSEMBLY

CROSS-REFERENCE TO RELATED INVENTIONS

Reference is hereby made to the following applications and patents that relate to the present invention: U.S. patent application Ser. Nos. 897,936 filed on Aug. 19, 1986, now U.S. Pat. No. 4,791,937; 921,471 filed on Oct. 22, 1986, now U.S. Pat. No. 4,799,494; and 222,096 filed on July 18, 1988, and U.S. Pat. Nos. 532,.935, 4,617,940, 4,702,260 and 4,766,906. The disclosure of each of these applications and patents is expressly and fully incorporated hereunto by reference.

FIELD OF THE INVENTION

The present invention relates to a flexible assembly for collecting tissue specimens such as for biopsy examinations. The assembly is designed for use with any type of inter-body scope, such as, for example, bronchoscopes, cystoscopes, laparascopes and proctoscopes or any other fiberoptic scope that can be used to enter body cavities and permit the undertaking of medical procedures or collection of tissue specimens. The present invention permits the obtaining of tissue specimens for biopsy purposes. Such specimens are collectable from tumors or lesions exposed directly on the interior of the body cavities and organs into which such a scope can pass. More importantly, the present invention permits collection of tissue specimens from sites located on the outer surfaces of tissue walls of various body cavities or organs through non-invasive procedures.

BACKGROUND OF THE PRESENT INVENTION

Prior to my earlier inventions, as cross-referenced above, invasive procedures would be required to obtain tissue specimens from tumors, lesions or other growths located within the body but not directly exposed within a body cavity. Invasive procedures included surgical opening of the body to expose the tumor or growth, or by the use of stiff, large gauge needles, such as disclosed in U.S. Pat. Nos. 3,628,524 and 3,630,192 to Jamshidi, which allowed percutaneous entry to the desired site.

Figures 1, 2:
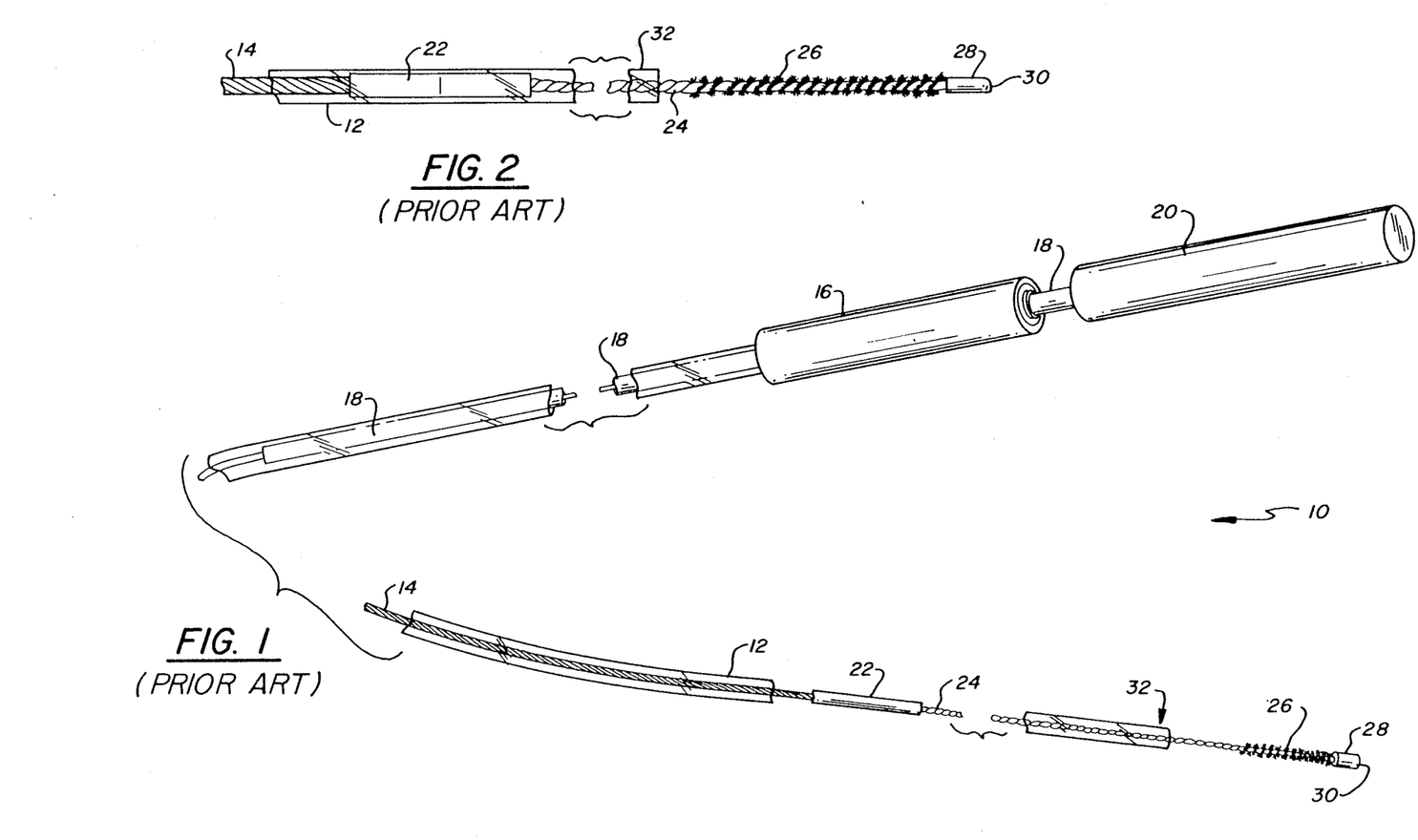
FIG. 1 is a perspective view of a prior art bronchial cytology brush.
FIG. 2 is an enlarged view of the distal end of the cytology brush shown in FIG. 1.

My earlier inventions have focused upon the use of needles as the means for collecting tissue samples. However, other forms of tissue collection devices have use as well. Brushes and a brushing technique have been used for many years with endoscopes for the collection of tissue specimens located directly on interior walls of the lungs. One example of a bronchial or cytology brush, manufactured by Mill-Rose Laboratories, Inc. of Mentor, Ohio is shown in FIGS. 1 and 2.

This brush is slidably retained in a hollow flexible tube and was connected to the distal end of a cable. The proximal end of the cable was connected to a handle which allowed the user to slide the brush relative to the tube so that the bristles could be moved over tissue exposed within the particular body cavity into which access could be easily reached. No seal is provided between the tube, brush, cable or handle. The distal end of the tube itself was not provided with any means for aiding the placement of the device within the body and there was no way to remove tissue from within the tube. Further, the brush was not capable of insertion into or through tissue. In fact, tissue penetration was specifically prevented by the presence of a blunt shaped member fixed to the device at the distal end of the brush.

SUMMARY OF THE PRESENT INVENTION

The present invention relates to an improved brush type tissue specimen collection assembly for use with various types of endoscopes. The assembly includes a brush collection device designed to penetrate tissue in order to collect tissue specimens from tumors, lesions or growths located on or adjacent the outer surfaces of the tissue walls of body cavities or organs. Such body cavities and organs include the lungs, bronchus or trachea, the stomach, the bladder, the abdominal cavity or other organs or body cavities that are subject to fiberoptic-/endoscopic inspection procedures. This allows the brush to reach tissue sites not previously available to the prior brush device. The sealing of the parts of the device permits the use of flushing fluids to irrigate the specimen collection site, as an aid in tissue collection, the flushing of tissue specimen material from within the outer catheter, and/or the connection of aspiration means through the outer catheter directly to the collection site. The catheter is also easily movable through an endoscope due to the use of a smooth tip member at the distal end of the outer catheter making the assembly, and in particular the tip, able to be correctly positioned at the desired location so that even a small tumor can be penetrated under fluoroscopic guidance.

Other objects, features, and characteristics of the present invention, as well as the methods and operation and functions of the related elements of the structure, and to the combination of parts and economies of their manufacture, will become apparent upon consideration of the following description and the appended claims with reference to the accompanying drawings, all of which form a part of this specification, wherein like reference numerals designate corresponding parts in the various figures.

DETAILED DESCRIPTION OF THE PREFERRED EXEMPLARY EMBODIMENT OF THE PRESENT INVENTION

The Prior Art

Turning first to FIG. 1, the drawing shows a prior art bronchial cytology brush for collecting tissue by simply moving the brush against tissue exposed directly within the ling. The brush assembly, generally indicated at 10, includes an outer catheter or tube 12 within which is positioned a control wire 14. Catheter 12 is connected to a hollow cylindrical handle member 16. Wire 14 is connected to a shank 18 which is itself connected to another handle portion 20. Shank 18 extends through handle portion 16, as shown in FIG. 1, and on into a portion of the proximal end of catheter 12. The connection between wire 14 and shank 18 is by crimping shank 18 about wire 14.

A connector 22 in the form of a hollow cylinder is crimped to the distal end of wire 14, as well as to proximal end of a second wire 24 comprised of twisted strands in which bristles 26, forming a brush, have been formed. The distal end of the wire strand 24 is provided with an end cap 28 soldered or otherwise fixed in place directly on wire 24. End cap 28 is in turn is provided with a blunt end 30. The distal end of catheter 12, indicated at 32, is comprised simply of the same plastic material as the main body of the catheter 12.

The blunt end cap 28 at the distal end of wire 24 is provided to help assure that tissue is not penetrated or injured by movement of the brush past the tumor and was specifically not intended to penetrate skin or tissue. Rather, this device was used by inserting the brush in a bronchoscope and the brush area 26 was simply rubbed against tissue exposed within either the bronchial passage or the lungs. Some amount of tissue would be collected within the bristles by this brushing contact. After samples had been obtained, the brush would be retracted into the distal end of catheter 12 by withdrawing handle portion 20 outwardly away from handle portion 16. Then the entire assembly would be withdrawn from the bronchoscope. Once removed from the bronchoscope the brush would be pushed outwardly from the distal end and samples could then be removed from brush 26 by shaking the brush against a collection surface or within a container filled with a liquid allowing the tissue specimens to leave the confines of brush 26. There was no way to collect tissue material located within the tube 12.

The Present Invention

Turning now to FIGS. 3 through 9, the present invention, generally indicated at 100, includes a proximal end portion generally indicated at 102, a distal end portion generally indicated at 104 and a stop assembly generally indicated at 106.

Figure 4:
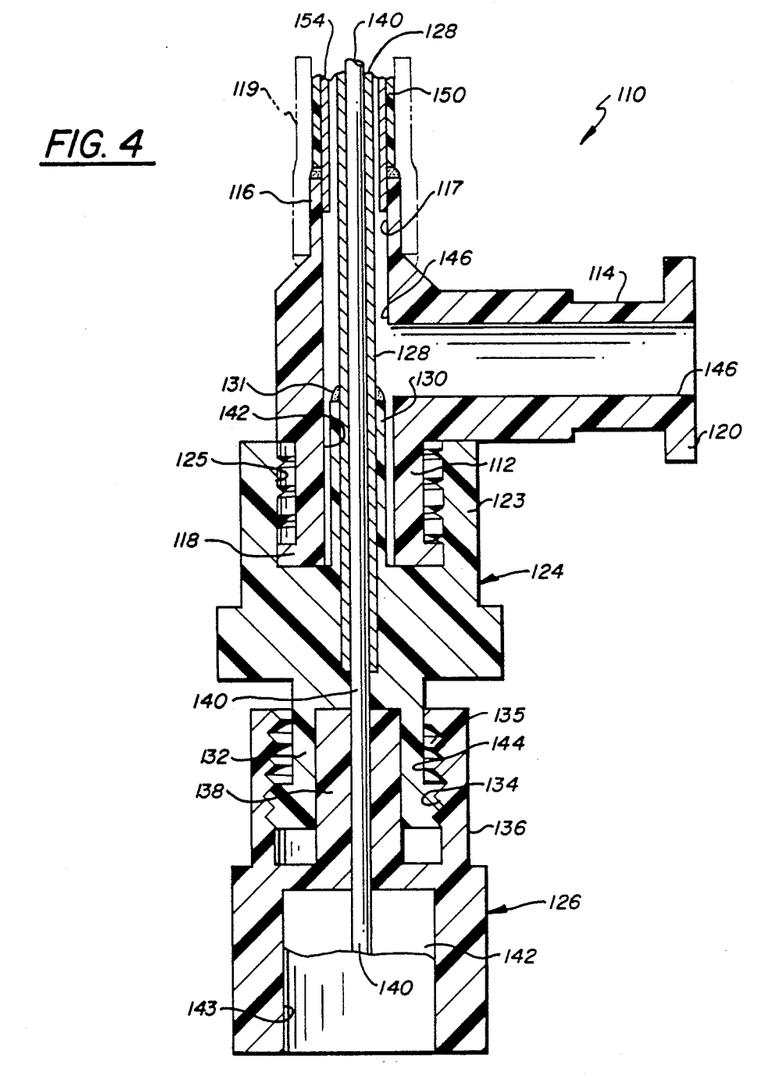
FIG. 4 is a cross-sectional view of the control apparatus at the proximal end of the present invention in a closed condition.

Turning first to the proximal end 102, this includes a conventional two directional leur lock, generally indicated at 110, having three outwardly extending connection members 112, 114 and 116, respectively. Connections 112 and 114 each terminate with nipple members 118 and 120, respectively, for threadedly engaging a conventional connector member as is used to connect needles on syringes. It should be understood, however, that any convenient connection arrangement can be used. Nipple 120 can be connected to a suitable source of fluid or to an aspirating means as shown at 122 which can, for example, be a syringe or other form of a device for injecting or withdrawing fluids from within the catheter device or for supplying a desired aspirating force. Nipple 118 is arranged to be threadedly engaged by a first coupling cap 124 that is provided with a hollow cylindrical portion 123 in which internal threads 125 are formed as shown in FIG. 4. A second coupling cap 126 is provided axially outwardly from cap 124 and, as will be explained below, is designed for connection to the first cap 124.

An elongated, hollow cylindrical metal conduit 128 is connected to the first cap 124 and extends outwardly from a cylindrical member 130 spaced radially inwardly from the hollow portion 123. The connection between cap 124 and conduit 128 can be accomplished by any suitable adhesive or conduit 128 can be molded in place together with cap 124. The leur lock connection 112 includes a hollow interior passageway 142, connection 114 includes a hollow interior or passageway 146, and connection 116 includes a hollow internal passageway 147.

FIG. 4 shows the leur lock assembly 110 and the caps 124 and 126 in their closed positions. With cap 124 in this condition the cylindrical member 130 lies within passageway 142, threads 125 engage the threaded exterior of connection 112 and the end wall of connection 112 abuts the interior wall of cap 124.

Figure 3:
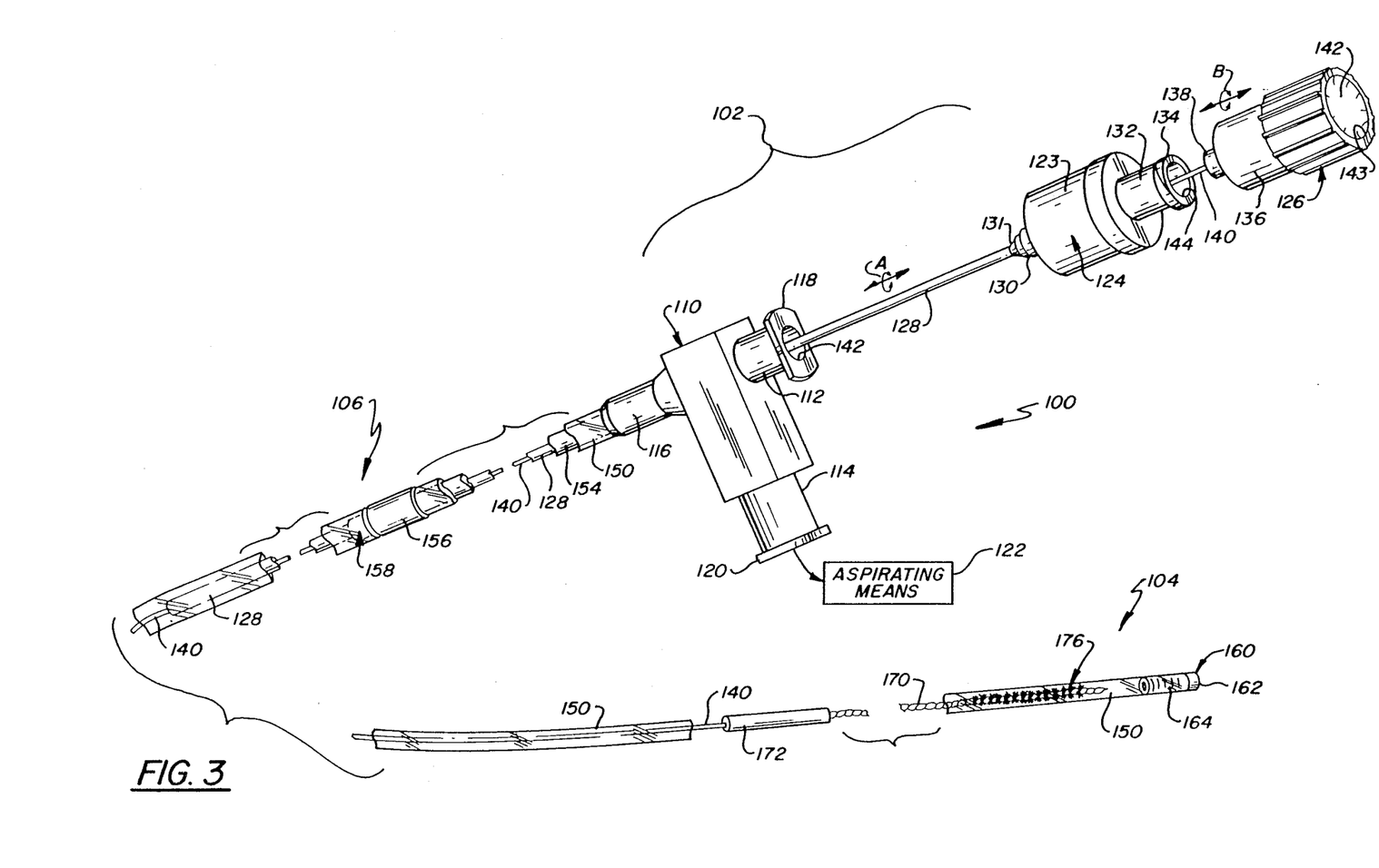
FIG. 3 is a perspective view of the improved endoscope device according to the present invention with the control apparatus in an open condition and with the brush retracted within the outer catheter inwardly of the distal end thereof.

FIG. 3 shows these same control elements in an open and slightly pulled apart condition.

The first coupling cap 124 also includes a second cylindrical portion 132, which extends axially in a direction opposite that of member 130 and from the opposite end of cap 124. Portion 132 has a hollow interior well 144 and a threaded exterior rim 134 which is received within the threaded interior 135 of the lower portion 136 of the second coupling cap 126. It should be noted that the hollow well 144 is not connected to the hollow interior portion 123 of the first cap 124. Rather, a wall seals one from the other and only stylet 140 passes through that wall via an aperture provided therein and through the interior of conduit 128 which is sealed to and within member 130.

The second coupling cap 126 also includes an axially extending cylindrical mounting member 138 spaced radially inwardly from the interior of the threaded interior of portion 136. Member 138 has a diameter designed to fit snugly within well 144 as shown in FIG. 4. The flexible stylet 140 passes through member 138 and is secured to cap 126, so that it will move therewith and be controllable thereby. Specifically, stylet 140 is secured within a hollow, outwardly opening rear recess or well 143 of cap 126 such as by adhesive 142 placed in well 143. It should be understood that the external diameter of stylet 140 has a tight sliding fit within the internal diameter of conduit 128. Consequently, when both caps 124 and 126 are in their closed position, as in FIGS. 4 and 5, fluid entering leur lock 110 will pass through passage 140 and directly into catheter 150. With suitable sealing it will not leak backwards between stylet 140 and conduit 128 or between conduit 128 and member 130. This assures that there will be a fluid seal within leur lock 110 and caps 124 and 126 will provide an effective seal for fluids moving there through.

An outer catheter 150 is secured to connection 116 of leur lock 110 by any convenient means such as an adhesive shown at 152 in FIG. 4. This connection between catheter 150 and connection 116 can be improved and strengthened by use of an additional overlapping sheath of material, as shown in phantom in FIG. 4 at 119. Sheath 119 is preferably comprised of a plastic, perhaps a fairly stiff plastic, but other materials could also be employed since its utility is to strengthen the joints that are connected together at that point. Sheath 119 can also be glued or otherwise sealed in place.

An elongated, hollow cylindrical metal member or conduit 154 is attached to connection 116, specifically within passageway 147 where it is glued or otherwise fixed to the interior surface 117. This provides support for the outer catheter 150 in the area adjacent leur lock 110, it provides a gripping point for the user, it prevents the collapse of catheter 150 when this area is gripped and also aids in positioning the stop means. Cylindrical member 154 extends axially along the interior of conduit 150 and terminates an inch or two beyond leur lock 110.

The invention also includes a stop assembly to control and limit the range of axial sliding movement permitted for conduit 128. This stop assembly includes a stop band 156, preferably metal, is crimped about the exterior of the outer flexible catheter 150. This crimping must be carefully controlled as it is not desirable to crimp band 156 so much that the catheter's interior is constricted beyond that necessary to provide the desired stopping function. The stop assembly also includes a separate stop member 158 is secured to conduit 128 by soldering, adhesive, crimping or any other convenient method that will fix member in place. In terms of assembly, band member 156 is not crimped in place about catheter 150 until stylet 140 and member 128, with stop member 158 having been previously fixed in place, have been inserted through leur lock 110 and conduit 154 on catheter 150.

Figure 8:
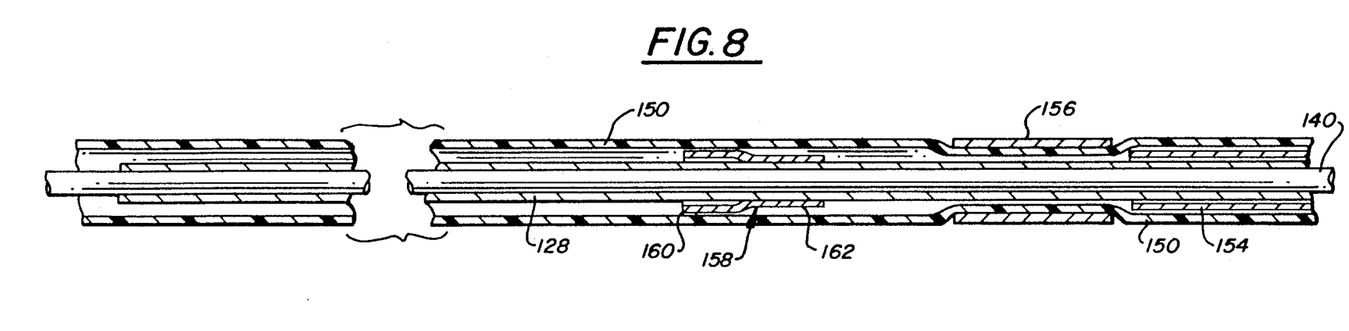
FIG. 8 is a diagrammatic cross-sectional view of the catheter showing a stop mechanism for the stylet in an open position.
Figure 9:
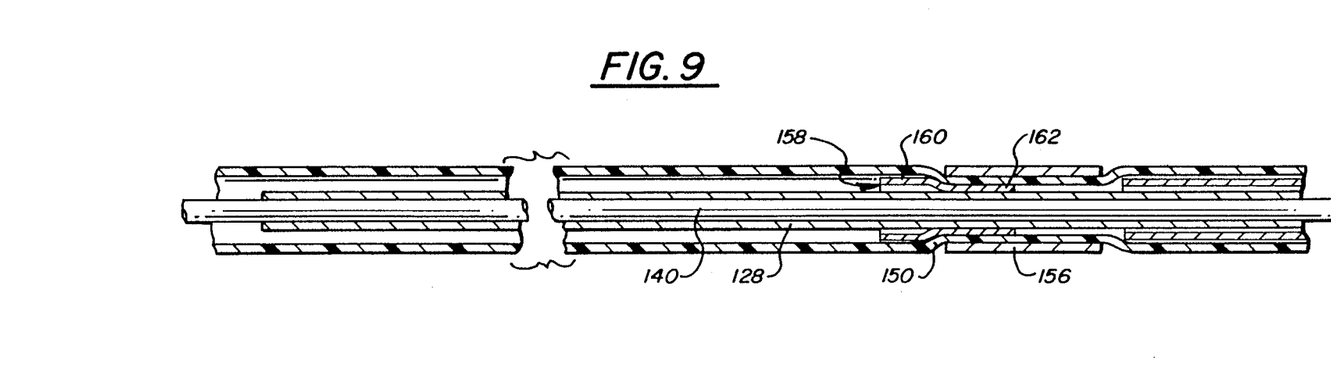
FIG. 9 is a cross-section similar to that of FIG. 8 but showing the stop in a closed position.

With reference to FIGS. 8 and 9, FIG. 8 shows the stop assembly in its open condition. Stop member 158 is comprised of a first portion 160 having an outer diameter less than the inner diameter of outer catheter 150 so that a fluid passageway is defined therebetween. The diameter of portion 160 is also less than the internal diameter of conduit 154. A second portion 162 extends toward the proximal end of the assembly and has a still further reduced diameter so that it is less than the diameter of portion 160 yet sized to fit within the opening defined within the crimped portion of catheter 150 following the mounting of band 156.

As shown in FIG. 9, with the stop assembly in its closed or stopped condition, the placement of band 156 will sufficiently change both the outer and inner diameter of the outer catheter 150 so that the portion 160 of stop member 158 will not be able to pass axially beyond band 156.

Stop member 158 could be comprised of only a band type member equal to the dimensions of portion 160, thereby omitting the reduced diameter portion 162. The only requirement of stop member 158 is that it have a diameter sufficiently larger than the reduced diameter of the outer catheter 150 effected by the crimping of band 156 therearound.

The distal end of outer catheter 150 includes an outer metal slip tip, generally indicated at 160, which includes a smooth rounded exterior surface 162 and a threaded or grooved exterior portion 164 therebehind for engagement with the interior of outer catheter 150.

Figure 6:
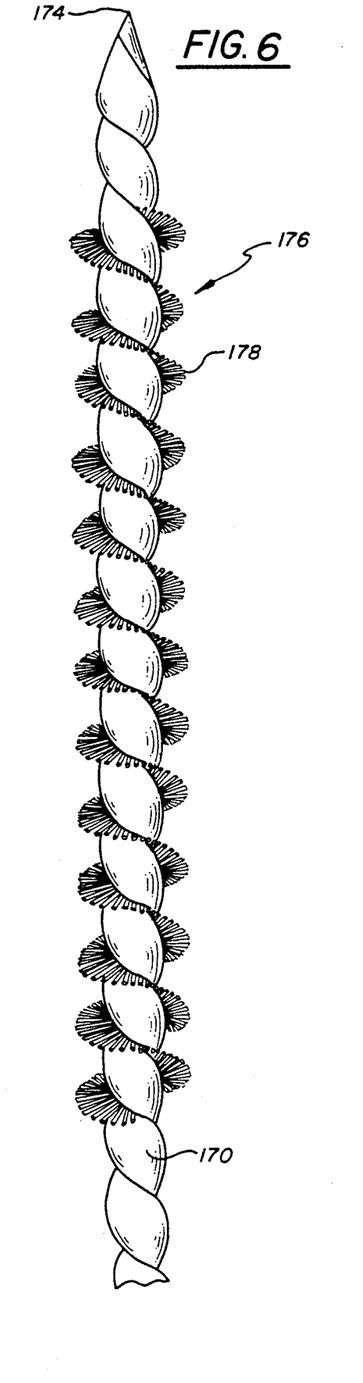
FIG. 6 is an enlarged view of the brush collector according the present invention.
Figure 7:
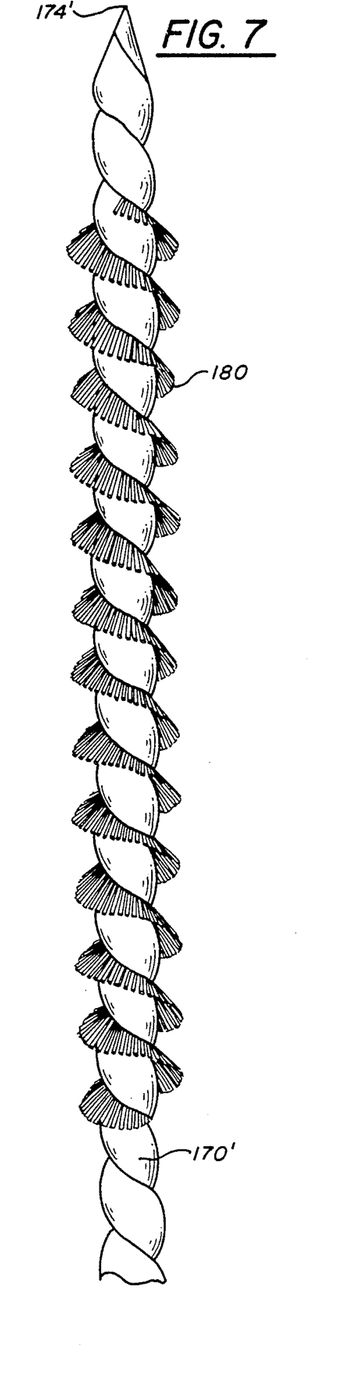
FIG. 7 is an enlarged view of a modified brush structure.

The distal end of stylet 140 includes a wound wire member 170 connected to stylet 140 by means of a crimped, cylindrical connector 172, and a brush generally shown at 176. The outer diameter of connector 172 is also less than the inner diameter of outer catheter 150 so that a fluid passage also exists between the interior of the catheter and that connection. Stylet 140 can be comprised of a solid flexible steel wire, a wound cable or any other similar material that can be used to apply axial force to the distal end of the stylet. The wound wire 170 terminates in a sharped, needle type point 174, as shown in FIGS. 6 and 7. This is a significant departure from other brush arrangements and actually permits penetration by the brush into and through tissue. Wire 170 is formed from two wires wound over one another so that brush 176 can be formed therewith as those wires are wound. Such a formation is conventionally made and further description thereof is not believed to be required. As shown in FIG. 6, a first embodiment of the brush includes bristles 178 that preferably extend substantially perpendicular relative to the axis of the wound wire 170. Bristles 178, preferably comprised of a sterilizable, plastic material, begin approximately 2-3 mm from the sharpened tip although other dimensions could be used. The bristles preferably extend approximately, for example, 10-15 mm along the length of the wound wire 170. This length could be modified to suit various collection or tissue situations. An alternative configuration is shown in FIG. 7 where bristles 180 extend from wire 170' in a direction angled more rearwardly toward the proximal end of the assembly. This alternative embodiment also includes a sharpened, needle like tip 174'.

Once the tip 174 or 174' at the distal end of the brush has penetrated into tissue, bristles 178 or 180 would brush through the incision area made by tip 174 or 174' and into the interior of the tumor or lesion. Through repeated backward and forward strokes within that incision area, controlled by manipulating cap 126, tissue specimens will be collected by, on and within the bristles. In the FIG. 7 embodiment, by having bristles 180 extend more rearwardly, additional collection force would be provided on the rearward stroke as wire 170' was withdrawn from the incision made by tip 174'.

The tip of the distal end of the brush can be sharpened to a needlepoint or other varying degrees of sharpness so that it can easily penetrate deep into a tumor or through the bronchial wall, through the intestinal wall or through the tissue wall of the body cavity to reach a tumor positioned on the outside of the tissue wall. Such a tumor would not be reachable by the prior art brush assembly as shown in FIG. 1 since that brush would only be able to move against the exposed surface of a tumor inside a lung or inside an intestinal tract. It would not be possible to use that brush assembly to penetrate either the bronchial wall or the wall of an intestine to extend into a tumor positioned on the opposite side of that bronchial or intestinal wall.

The rounded metal tip 160 attached to a distal end of the outer catheter 150 provides a smooth surface that will easily and smoothly pass through an endoscope as well as a guidable member that can be seen on x-ray or fluoroscopic equipment so that the correct placement of the tip on the tissue wall exactly next to the tumor location can be guided under use of a fluoroscope and the tumor can be easily investigated.

The brush 176 is movable by the operation of coupling cap 126 relative to the joint structure formed by having cap 124 locked to leur lock 110. Also, stop 156 is positioned so that when the caps 124 and 126 are connected together and cap 124 is disconnected from leur lock 110 and retracted, as shown in FIG. 3, the tip of the brush 176 will be properly withdrawn within catheter 150, that is inside or adjacent the metal tip 160. This assures the brush will not interfere with the sliding of the entire assembly through the endoscope and that the brush will not be retracted too far into catheter 150.

Following the correct placement of the tip adjacent the tumor cap 124 will be connected again to the leur lock thereby re-establishing the brush position beyond the distal end of the catheter. The device can then penetrate through the tissue wall and pass into the tumor or lesion. Cap 126 can be retracted away from cap 124 so as to move the brush relative to the, catheter. Each movement will result in the collection of additional tissue specimens and when sufficient collection has occurred the brush can again be retracted into the flexible outer catheter 150. During this collection process it will be possible to either apply suction at the collection site or to inject an amount of a normal saline solution, for example approximately 5cc, through leur lock 110 and into and through the outer catheter 150, directly to the specimen collection site. This washing will assist in tissue collection. Following the tissue collection procedure and after the entire device has been removed from the endoscope, fluid can be forced through outer catheter 150 to flush any remaining tissue from within the catheter.

This type of flushing technique to remove specimens, not only from the brush but within the catheter, was not available with the prior art device. In practice, the extraction of specimens from the prior art brush was accomplished by extending the brush beyond the end of the catheter and shaking it into a container. Any specimen left inside the catheter of the prior art device would not be collectable for examination. This would of course, reduce the chance of positive diagnosis if significant tissue specimens remained within that catheter.

The present invention also permits the local area near the tumor to be washed by a normal saline solution or aspirated in order to obtain even additional specimens and to increase the diagnostic yield. This aspiration or flushing procedure can occur simultaneously with the movement of the brush within the incision, while the brush remains in that incision or after the brush has been partially removed.

Accordingly, the newly designed brush according to the present invention, including the needle tip, permits deep penetration into tumors as well as penetration through tissue walls of the body cavity being explored. Because of the presence of the metal tip at the distal end of the outer catheter 150, fluoroscopic guidance can be used to correctly pass the tip through an endoscope and properly position the tip adjacent the tumor.

Figure 5:
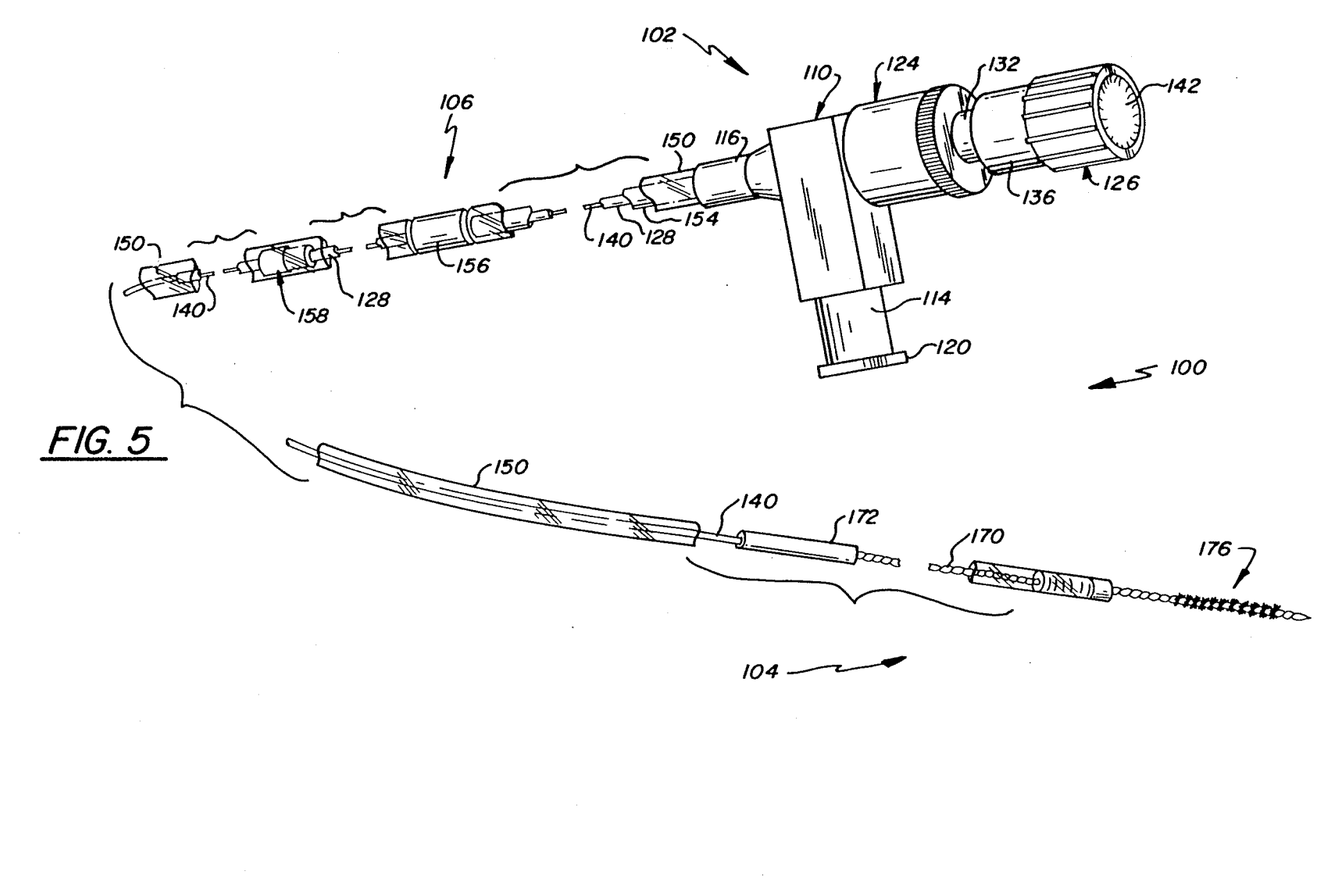
FIG. 5 is a perspective view of the present invention that is similar to FIG. 3 but with the control apparatus in a closed condition and with the brush extended beyond the distal end in an operating mode.

To summarize the method of using this invention, one would first assemble a device as shown and while coupling caps 124 and 126 together, cap 124 would be retracted from leur lock 110 so that the tip 174 of brush 176 was housed either inside the metal hub 160 or in catheter 150. The catheter 100 could then be inserted through the desired scope to a location guided by the fluoroscope with the tip 162 being properly positioned adjacent the tumor. Cap point 124 can then be moved to its locked position on leur lock 110, as shown in FIG. 5, so that leur lock 110, cap 124 and cap 126 are all locked together and the point of the brush and the brush itself lie within the tumor. Then by uncoupling cap 126 from cap 124, the brush can be retracted and advanced within the tumor or lesion. By using saline solutions, such as 5 to 10 cc of a normal saline, through the side extension 114 of leur lock 110, local washing can be obtained from the lesion. Further, suction can be applied to the collection site through the leur lock assembly. Then, brush 170 can be retracted into catheter 150 by unlocking and retracting cap 126 from cap 124 or by simply unlocking cap 126 if cap 124 had already been unlocked before retracting and advancing movement. It should also be understood that advancing and retracting of the entire catheter structure could be accomplished with leur lock 110, cap 124 and cap 126 all in a locked condition. However, prior to withdrawing the device 100 from the endoscope the brush needs to be drawn inside catheter 150. To accomplish this, either cap 126 needs to be unlocked from cap 124 to allow stylet 140 to be withdrawn or cap 124 needs to be unlocked from leur lock 110 to allow conduit 128 and stylet 140 to be retracted. Retraction of conduit 128 can proceed until stop member 158 hits the stop band 156. Once the entire device 100 is removed from the endoscope, specimens can be flushed into a container by again injecting normal saline solution through leur lock 110. Caps 124 and 126 can also be reconnected to leur lock 110 so that the brush will again extend outwardly away from the distal end of the device allowing tissue specimens to be removed.

The outer catheter 150 is preferably constructed from suitable surgical plastic that can be sterilized. The leur lock and the control caps are also preferably made from similar surgical plastic. Hollow members 128 and 154 are preferably stainless steel and are about, for example, 95–100 mm and 15–25 mm long, respectively. Where the total length of the assembly is about 140 cm, the stroke of the stylet, as controlled by the stop means, can be, for example, about 25–30 mm and the tip 160 is about 6–8 mm in length. The outer diameter of catheter 150 is about 2.0 mm and the inner diameter is about 1.5 mm. The gauge of stylet 140 is about 24.

Figure 10:
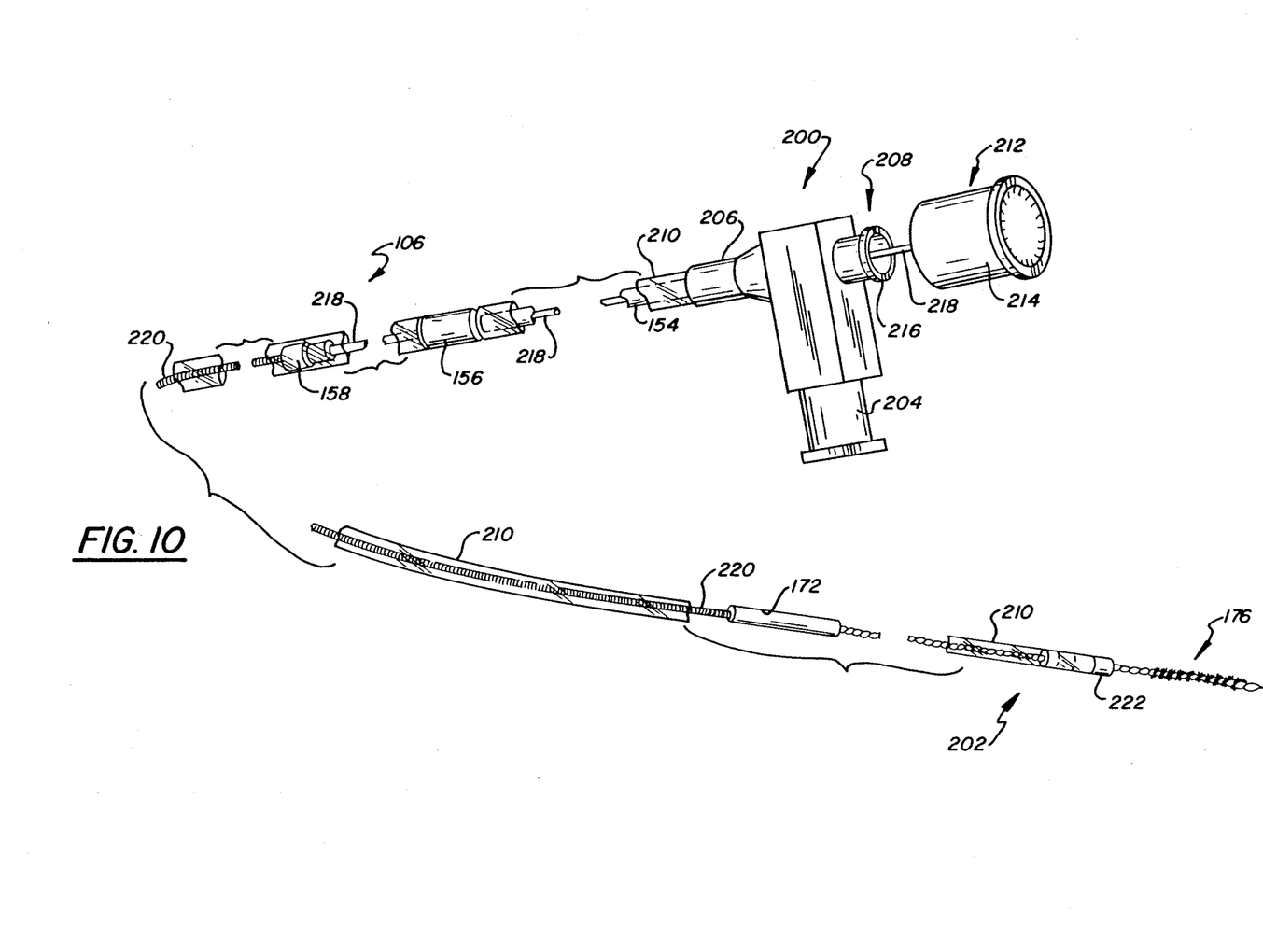
FIG. 10 is a perspective view of the present invention showing a modified form of the control cable.
Figure 11:
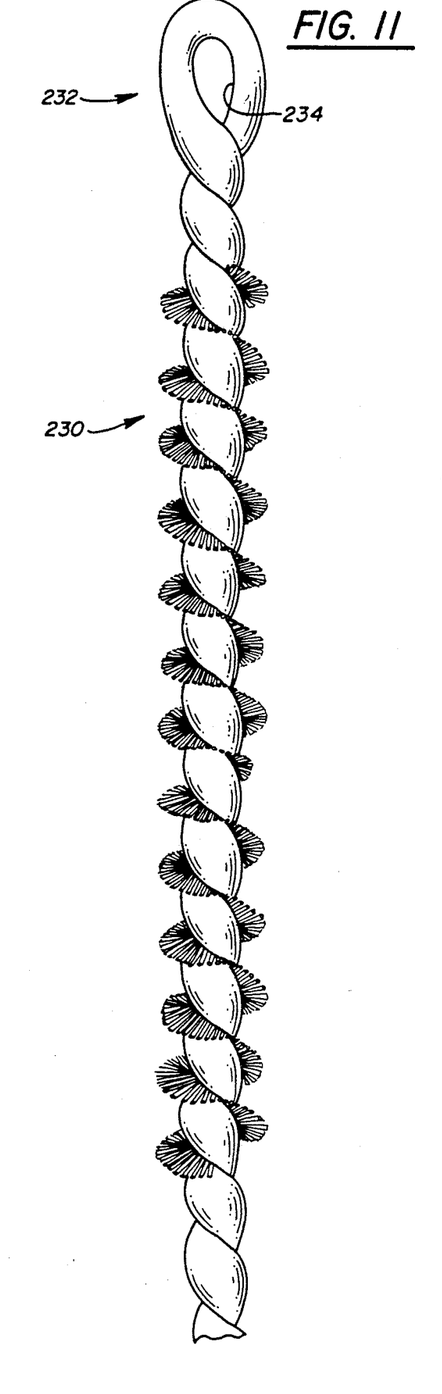
FIG. 11 is an enlarged view of a still further modified brush structure.

Turning now to FIGS. 10 and 11, another embodiment of the present invention is set forth. This embodiment of the tissue collection or flexible endoscope assembly, like those previously described, also includes a proximal end comprised in part of a leur lock generally indicated at 200, a distal end generally indicated at 202, and an interconnecting catheter assembly.

Leur lock 200 includes three connection members generally indicated at 204, which is the main connection for providing other aspirating fluids for connection of a vacuum, 206 and 208. Connection 206, like 116 in the earlier embodiments, is provided with a hollow interior, similar to that shown at 147 in FIG. 4, in which a conduit 154 is received and sealed thereto by any convenient means, such as by adhesive or by being molded integrally with the leur lock. Connection 206 also provides a connection point for an outer catheter 210 which, after having been slid over conduit 154, can be glued or otherwise sealed to the end of connection 206. This was also the method of connecting the outer catheter 150 and connection 116 in the earlier embodiments.

The proximal end also includes a control cap 212, which includes a hollowed cylindrical portion 214, similar to portion 123 in the first cap 124 of the embodiment shown in FIG. 3. The interior wall of portion 214 is threaded to receive the threaded portion 216 of connection 208.

Cap 212 provides control over a stylet 218 which is suitably connected to cap 212 by adhesive, in a manner similar to the way in which stylet 140 was connected to cap 126. Stylet 218 passes through the interior of connection 208, through leur lock 200 and on through the conduit 154. A stop member 158 is attached adjacent the distal end of stylet 218 and will, as in the earlier embodiments, cooperate with a stop band 156 that is crimped about the outer catheter 210. Positioned between stop member 158 and a cylindrical connector 172, which serves to attach brush 176 to the assembly, is a helical spring 220. It is preferred that the proximal end of 220 be crimped or otherwise fixed within stop member 158 and that a similar connection be provided between the distal end of spring 220 and connector 172. However, the particular method of attaching spring 220 to stylet 218 and to the distal end of the assembly is not critical and any convenient method may be employed.

Spring 220 is constructed so that it can transmit axial forces supplied by cap 212 to the tissue collection device or structure at the distal end, such as to a brush 176. Spring 220 has a length slightly longer than the length of outer catheter 210 and when cap 212 is closed and connected to leur lock 200, with portion 214 threadedly engaged on portion 216, the spring will be under compression and provide a relatively rigid connection or control link between cap 212 and the tissue collection structure at the distal end of the endoscope assembly. Where that structure is comprised of brush 176 that brush will then be fully extended beyond the hub member 222 located at the distal end of catheter 210. Conversely, when cap 212 is disconnected from connection 208 and stylet 218 is fully withdrawn from the assembly, as permitted by stop 156, brush 176 will then lie within the distal end of the outer catheter and the point of brush 176 will lie within hub member 222. When cap 212 is disconnected from leur lock 200, the compression load on spring 220 will have been removed and it will, accordingly, be very flexible. Consequently, the entire catheter assembly will likewise be more flexible than would be the case where a stylet, comprised of a metal wire like strand, was used as the control link and where it passed all the way to connection 170 from cap 212. Spring 220 assures that the overall flexibility of the assembly will be substantially increased and indeed permits much tighter or sharper turns to be negotiated by an operator whether within the patient or within the endoscope assembly.

As an alternative embodiment for brush 176, reference can be made to FIG. 11. Here the end of the brush assembly, identified at 230, is provided with a loop type distal end structure 232. This looped end is rounded off and will in some instances provide a safer tip as well as the additional advantage of permitting the retrieval of specimen samples embedded within the opening 234.

Figure 12:
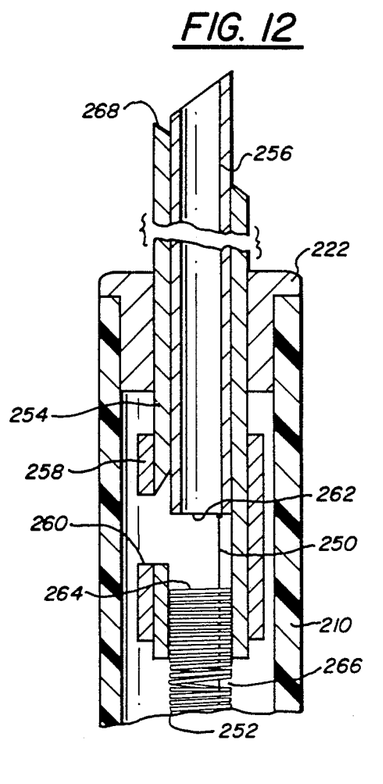
FIG. 12 is an enlarged cross-sectional view of an alternative embodiment for the distal end of the device shown in FIG. 10 using the modified control cable.

Turning now to FIG. 12, this figure shows the distal end structure of another embodiment. The proximal end structure would be both as shown in the FIGS. 3 and 5 embodiments, where two end caps were employed, and like the embodiment of FIG. 10 insofar as that used a spring connection between the leur lock and the distal end tissue collection structure. The innermost end cap would be connected, in the manner just discussed above with respect to FIG. 10, by having stylet 218 passing through the leur lock and be connected to a stop member 158 as well as connected to a spring 252. In this instance both the stylet 218 and stop member 258 will be hollow so that an elongated passageway is defined therewithin leading through to the distal end of the assembly. A stylet, similar to that shown at 140, would then be able to be pushed along and through that passageway and through the hollow interior of the coil spring 252. Such a stylet is shown in FIG. 12 at 250.

In this embodiment, however, the tissue collection assembly at the distal end is not comprised of a brush but rather a double needle assembly comprised of an outer needle 254 and an inner needle 256. The distal end of spring 252 is secured within the internal diameter of the outer hollow needle 254 by being crimped, soldered or otherwise fixed in place. The distal end of stylet 250 is itself secured to the proximal end of the second or inner hollow needle 256 by soldering or other convenient means. Outer needle 254 is provided with a stop member 258 that will limit its movement beyond hub 222 when that stop 258 abuts the interior of hub 222. Outer needle 254 is also provided with an opening 260 that extends through both the stop member 258 and the needle side wall. Accordingly, an opening is provided to connect the passageway defined between outer catheter 210 and about the exterior of spring 252 into the interior of outer needle 254. When the proximal end of the innermost needle 256 lies above or adjacent opening 260, then this passageway along catheter 210 will be connected into the interior of the inner needle as well via its proximal end which is itself open. By operating the end caps in the manner described above, with respect to end caps 124 and 126, when end cap 124 is closed spring 252 is placed under compression. This will move the outer needle 254 axially toward the distal end of catheter 210 until stop 258 abuts the interior of hub member 222. At that time, spring 252 can then be axially loaded and compressed to the point that it becomes a substantially rigid member or connection link. End cap 126 controls the axial movement of stylet 250 and the axial position of inner needle 256 within outer needle 254. When the two end caps are connected together, the distal end of the inner needle 256 extends outwardly beyond the distal end of the outer needle 254. If the outermost cap 126 were disconnected from cap 124, then inner needle 256 could be retracted so that its tip was positioned inside the tip of outer needle 254. The retraction of inner needle 256, however, will be limited by the length of outer needle 254 and by the position of spring 25 within the proximal end of outer needle 254. Thus, when inner needle 256 is fully retracted within outer needle 254, its proximal end 262 will engage the distal end 264 of spring 252. Because there is no opening cut within the side wall of the inner needle 256, as shown in FIG. 12, retraction of the inner needle 256 to the point it engages spring 252 it will close opening 260. However, a passageway can still provided from the leur lock 200 to the interior of the hollow needles 256 and 254 by means of a gap 266 that can be formed in spring 252 by purposely skewing or deforming part of the coil spring 252. Such a gap need not be positioned directly adjacent the distal of the spring but could be located virtually anywhere along the length of the spring 252 since the spring is itself hollow. Such a gap will also not prevent spring 252 from being loaded axially. Accordingly, fluid or suction passageways can still be provided from the leur lock assembly to and through the hollow interior of needles 254 and 256 to the tissue collection site.

This construction not only provides a first hollow needle within a second hollow needle but provides a separate way of developing suction and/or fluid passageways from within the outer catheter into the interior of that hollow needle structure. Further, by using this spring 252, the desired rigidity of the device when taking samples is not decreased but surprisingly, when the spring is under compression and fully loaded with stop 258 in contact with hub member 222, the outer hollow needle 254 will be under rigid conditions able to withstand the repeated penetrations into tissue that are required in order to obtain the desired sampling. When the spring 252 is uncompressed, it will be much less rigid and more flexible than would a combination of a separate inner catheter together with the interior stylet used to control the inner needle. The overall flexibility of a structure including the spring plus an internal stylet will be much more flexible and thus more easily positioned within the patient. By providing the gap within the spring or perhaps several gaps along the length of the spring, the ability to place the needle under compression will not be impaired and the desired fluid passageway will be absolutely established between the leur lock and the interior of the outer hollow needle structure when it is in position within a patient and the inner hollow needle has been retracted.

It should be understood, that while the tip 268 of the outer hollow needle 254 has been shown as being pointed and sharpened in a conventional way, that needle could also have a more circular outer end, or an outer tip, that was sharpened in any other manner that would accomplish the desired purpose of collecting tissue specimens. The inner hollow needle 256 could, for example, be a 21 gauge needle, whereas the outer hollow needle 252 could be a 19 gauge needle, so that it would receive the outer diameter of the inner needle 256 therein in a sliding relationship. Further, it should also be understood that the tissue collection system could delete the innermost needle and its control stylet.

Figure 13:
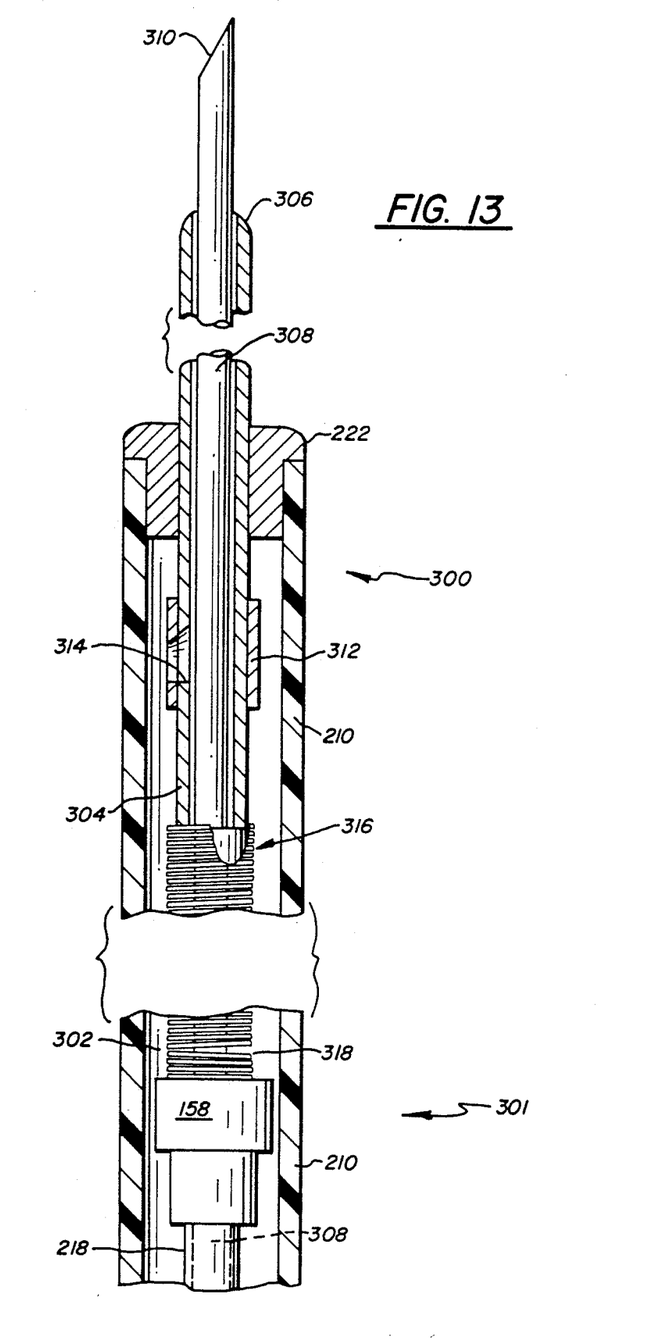
FIG. 13 is an enlarged cross-sectional view of still another embodiment of the device shown in FIG. 10 employing the modified control cable.

Turning now to FIG. 13, the distal end of the needle assembly is generally indicated at 300 and a portion of the proximal end is shown at 301. The proximal end is comprised of an outer catheter 210, ending with a distal hub member 222 as in the earlier embodiment. Similarly, a conduit 218 is provided as part of the proximal end and has stop member 258 secured to its distal end. Also included in this embodiment is a coil spring 302, as well as a hollow needle 304, which terminates at a sharpened tip 306. A wire stylet 308 extends from the proximal end of the assembly, through spring 302, needle 304 and terminates with a sharpened tip 310. Hollow needle 304 is also provided with a stop member 312 to control the axial extent to which it will move beyond distal end of hub 222. Needle 304 is provided with an opening in its side wall generally indicated at 314 to again establish a flow path from the passageway about spring 302 and from the leur lock (not shown). As shown in FIG. 13, because the opening is provided at the location of stop member 312, the opening also extends through that stop member. It should be understood, that the opening through the side wall of needle 304 can be provided at any location and depending on the design of stop member 312, the opening might only pass through the side wall of the needle. The spring 302 is shown as fitting around and being secured to the exterior of the proximal end of needle 304, indicated generally at 316. The manner of securing the spring 302 to needle 304 could be by solder or any other convenient means of making that connection. The only requirement is that the connection method should not close off the hollow interior of needle 304. It should be noted that by placing the spring on the outside, stylet 308 will have a sliding fit along the entire length of needle 304.

This embodiment would again employ a leu lock like 110 with two end caps similar to those described above at 124 and 126, with the innermost end cap 124 controlling conduit 218, spring 302 and needle 304, while the outermost end cap 126 would control the positioning of stylet 308. With the first or innermost end cap closed, stop member 312 would be in contact with hub member 222, spring 302 would be under a compression load and needle 304 would, accordingly, be sufficiently rigid held in place by the compressed spring to allow end 306 to penetrate the tissue of the patient. In order to assist initial penetration, stylet 308 could be in the position as shown in FIG. 13 so that its distal end 310 extended beyond the distal end 306 of needle 304. Following initial penetration by the stylet 308, it could then be retracted. If needle 304 were provided with a side wall opening 314, it is preferred that the distal end of the stylet be withdrawn such that it was positioned axially on the proximal side of the opening 314. In this way a passageway from the leur lock between and along the internal assembly and the outer catheter 210 would be provided directly into the hollow interior of needle 304 via opening 314. Alternatively, if the needle did not include a side wall opening, such as that shown at 314, one or more gaps as indicated at 318 could be provided within spring 302 so that a passageway would be provided interiorally of spring 302 upwardly along the stylet 308. With a 22 gauge needle 304, the internal diameter would then receive a 24 gauge stylet. Also by having stylet 308 with a smaller outer diameter than the inner diameter of the needle, comparable to a 23 gauge member, a suitable passageway would be provided between the exterior of that stylet and the interior of needle 304. Further, stylet 308 does not include any stop member so that it is possible to completely withdraw stylet 308 from within needle 304 and all or part of the interior of spring 302. Use of one or more gaps 318 within spring 302 would establish a fluid and suction passageway from the leur lock and the interior of catheter 210 into the interior of spring 302 and then directly to the interior of needle 304.

While the invention has been described in connection with what is presently considered to be the most practical and preferred embodiment, it is to be understood that the present invention is not limited to the disclosed embodiment, but, to the contrary, it is intended to cover various modifications and equivalent arrangements included within the spirit and scope of the appended claims.

WHAT IS CLAIMED:

1. A tissue collection system for use with endoscopes to collect tissue specimens from a site in the body, said system including an elongated outer flexible hollow catheter having distal and proximal ends, an elongated member slidably positioned within said hollow catheter, control means for controlling the sliding movement of said elongated member within said hollow catheter and for permitting the application of fluids or suction at the tissue collection site, said elongated member having a proximal end connected to said control means and a distal end terminating with a sharpened point, and brush means integrally formed with said elongated member adjacent said distal end for collecting tissue specimens, said brush means beginning at a point spaced a first predetermined distance along said elongated member from said sharpened point and extending along said elongated member for a second predetermined distance.

2. A tissue specimen collection assembly for use with a fiberoptic endoscope, said assembly including an outer flexible catheter, a flexible stylet, defining on axis along its length, slidably positioned within said outer flexible catheter, said outer flexible catheter having means defining a fluoroscopically observable distal end, said stylet having a distal end portion comprised of a wound wire member terminating at a distal end with a sharpened point and means defining a tissue specimen collection brush intertwined with said wound wire member, said brush being spaced a predetermined distance away from said sharpened point, said assembly including a proximal end having control means operatively connected to said outer flexible catheter and said stylet for controlling the sliding movement of said stylet relative to said outer catheter and for connecting a fluid supply to the interior of said outer flexible catheter.

3. The tissue collection assembly as in claim 2 wherein said brush includes bristles that extend substantially perpendicular to said stylet.

4. The tissue collection assembly as in claim 2 wherein said brush includes bristles that extend at an angle relative to the axis of said stylet.

5. The tissue collection assembly as in claim 2 further including stop means for controlling the movement of said brush relative to said outer flexible catheter.

6. The tissue collection assembly as in claim 5 wherein said stop means includes a retaining band positioned on said outer flexible catheter and a stop member secured to said control means within the interior of said outer flexible catheter.

7. The tissue collection assembly as in claim 2 wherein said flexible stylet includes a coiled spring extending along at least a portion thereof.

* * * * *